United States Patent
Wen et al.

(10) Patent No.: US 9,394,341 B2
(45) Date of Patent: Jul. 19, 2016

(54) EPTIFIBATIDE PREPARATION METHOD

(75) Inventors: Yongjun Wen, Chengdu (CN); Chuanbin Zhu, Chengdu (CN); Xiaoli Wang, Chengdu (CN); Yu Han, Chengdu (CN); Guangbin Tong, Chengdu (CN)

(73) Assignee: Chengdu Shengnuo BioTec Co., Ltd., Chengdu (CN)

( * ) Notice: Subject to any disclaimer, the term of this patent is extended or adjusted under 35 U.S.C. 154(b) by 0 days.

(21) Appl. No.: 14/388,026

(22) PCT Filed: Aug. 9, 2012

(86) PCT No.: PCT/CN2012/079882
§ 371 (c)(1),
(2), (4) Date: Sep. 25, 2014

(87) PCT Pub. No.: WO2013/117083
PCT Pub. Date: Aug. 15, 2013

(65) Prior Publication Data
US 2015/0299261 A1    Oct. 22, 2015

(30) Foreign Application Priority Data
Feb. 6, 2012    (CN) .......................... 2012 1 0025197

(51) Int. Cl.
| C07K 7/50 | (2006.01) |
| C07K 7/54 | (2006.01) |
| C07K 7/64 | (2006.01) |
| C07K 14/75 | (2006.01) |
| C07K 7/06 | (2006.01) |
| C07K 7/08 | (2006.01) |

(52) U.S. Cl.
CPC ... *C07K 7/64* (2013.01); *C07K 7/06* (2013.01); *C07K 7/08* (2013.01); *C07K 14/75* (2013.01)

(58) Field of Classification Search
None
See application file for complete search history.

(56) References Cited

FOREIGN PATENT DOCUMENTS

| CN | 1500805 A | 6/2004 | |
| CN | 101747412 A | 6/2010 | |
| CN | 101759776 A | 6/2010 | |
| CN | 1858060 B | 9/2010 | |
| CN | 102040652 * | 4/2011 | ............... C07K 4/06 |
| CN | 102040652 A | 5/2011 | |
| CN | 102584944 A | 7/2012 | |
| WO | 2011079621 A1 | 7/2011 | |
| WO | 2013117083 A1 | 8/2013 | |

OTHER PUBLICATIONS

Rinnová et al., Letters in Peptide Science (1999) 6, 15-22.*
Applied Biosystems, Technical Bulletin (1998) 1-12.*
English language abstract for CN101759776A (2010).
International Search Report for PCT/CN2012/079882 (Nov. 29, 2012).
Xiong et al, "Fmoc Solid-phase Synthesis and Purification of Eptifibatide", Journal of Xiamen University (Natural Science),vol. 46(1), pp. 100-103 (2007).

* cited by examiner

*Primary Examiner* — Marcela M Cordero Garcia
*Assistant Examiner* — Catherine Mader
(74) *Attorney, Agent, or Firm* — Caeser Rivise, PC

(57) ABSTRACT

An Eptifibatide preparation method with product purity of more than 99.5%, the method comprising: using a solid phase polypeptide synthesis method to prepare eptifibatide resin, conducting acidolysis on the Eptifibatide resin to obtain a crude Eptifibatide linear peptide product, oxidizing to obtain a crude Eptifibatide product, purifying and exchanging salt to obtain an Eptifibatide finished product; the method using the solid phase polypeptide synthesis method to prepare the eptifibatide resin is: using a solid phase coupling synthesis method to sequentially splice a corresponding protective amino acid or a segment in the following sequence onto amino resin, and obtaining the Eptifibatide resin: X—Y-Trp($R_1$)-Pro-Cys($R_2$)-amino resin, wherein $R_1$ is Boc or H, $R_2$ is Trt or Acm, X is Mpr($R_2$)-Harg($R_3$), $R_3$ is Pbf or H, and Y is Gly-Asp(OtBu).

15 Claims, No Drawings

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(7)
<220> FEATURE:
<221> NAME/KEY: MISC_FEATURE
<222> LOCATION: (1)..(1)
<223> OTHER INFORMATION: Mercaptopropionic acid
<220> FEATURE:
<221> NAME/KEY: MISC_FEATURE
<222> LOCATION: (2)..(2)
<223> OTHER INFORMATION: Homoarginine

<400> SEQUENCE: 1

Xaa Xaa Gly Asp Trp Pro Cys
1               5
```

EPTIFIBATIDE PREPARATION METHOD

FIELD OF THE INVENTION

The invention belongs to the technical field of preparation methods of polypeptide drugs, and particularly relates to a new preparation method of eptifibatide.

DESCRIPTION OF THE RELATED ART

Eptifibatide is a synthetic cyclic heptapeptide containing 6 amino acids and 1 deaminized cysteine (thiohydracrylic acid). The drug is invented based on a barbourin structure, and is a polypeptide found in snake venom of the *sistrurus m. barbouri*. Eptifibatide is a new glycoprotein IIb/IIIa inhibitor antagonist, and has advantages of strong antiplatelet action, rapid action and fewer adverse reactions by inhibiting the final common platelet aggregation pathway. The specific binding of eptifibatide and GP IIb/IIIa results from the peptide sequence of lysine-glycine-aspartate (KGD), and the only difference of one amino acid in the peptide sequence RGD of integrin ligand. The drug has high affinity and specificity to the GP IIb/IIIa receptor, and also has rapid dissociation rate. As a result, the elimination half life is short, the inhibition of eptifibatide to platelet is easily reversible, and platelet functions restore to baseline level within 2 to 4 h after stopping dripping the drug. Unlike abciximab, eptifibatide does not have immunogenicity, and the frequency of thrombocytopenia observed is similar to that of unfractionated heparin.

Eptifibatide is a specific GP IIb/IIIa receptor inhibitor, inhibits the aggregation of in vitro platelets of ACS patients in a dose dependent manner, and can inhibit the combination of fibroblast and adenosine diphosphate (ADP) activated platelets.

Inhibition of the product to platelet glycoprotein IIb/IIIa receptor is reversible, and the drug can be stopped immediately after any adverse reaction, with mild adverse reaction.

Eptifibatide has the following structure:

(SEQ ID NO: 1)

Mpr-Harg-Gly-Asp-Trp-Pro-Cys-NH$_2$ where Mpr is mercaptopropionyl residue and Harg is homoarginyl residue Reports on preparation methods of eptifibatide can be found both at home and abroad. An Fmoc solid phase synthesis method of eptifibatide was reported in Chinese patent CN200910247949, comprising the following methods: using amino resin as initial carrier resin, successively coupling protected amino acids, and using trifluoracetic acid (TFA) for acidolysis of the resulting peptide resin.

The structure of the product contains 1 Harg and 1 Gly, the product easily generates the following impurities during preparation due to own characteristics of Gly and features of the protected Harg structure during successively coupling Fmoc-Gly by a solid phase method: [+1Gly]-eptifibatide, [−1Gly]-eptifibatide and [−1Harg]-eptifibatide, thus significantly reducing purity of the crude product, and the impurities have similar polarity to eptifibatide, thus increasing difficulty in purification, being unable to effectively improve total yield of the product, affecting product purity and affecting medication safety.

SUMMARY OF THE INVENTION

A technical problem to be solved by the invention is to provide a preparation method of eptifibatide. The method uses a new fragment of protected amino acid, avoids the generation of impurities such as [+1Gly]-eptifibatide, [−1Gly]-eptifibatide and [−1Harg]-eptifibatide, improves the product yield and purity, presents high reaction efficiency, and is conducive to a scale solid-phase synthesis process.

The preparation method of eptifibatide of the invention comprises preparation of eptifibatide resin by a solid phase polypeptide synthesis method, acidolysis of the eptifibatide resin to obtain crude linear peptide eptifibatide, oxidation of the crude linear peptide eptifibatide to obtain crude eptifibatide, and purification and salt exchange of the crude eptifibatide to obtain finished eptifibatide, wherein the method for preparing the eptifibatide resin by the solid phase polypeptide synthesis method comprises successively coupling a protected amino acid or fragment corresponding to the following sequence on amino resin through a solid phase coupling synthesis method to obtain the eptifibatide resin:

X—Y-Trp($R_1$)-Pro-Cys($R_2$)-amino resin where,
$R_1$ is Boc or H;
$R_2$ is Trt or Acm;
X is Mpr($R_2$)-Harg($R_3$), $R_3$ is Pbf or H; and
Y is Gly-Asp(OtBu).

As a preferred solution of the invention, the solid phase coupling synthetic reaction is carried out once only to couple an X fragment, and the Fmoc-protected amino acid or fragment for coupling is Mpr(Trt)-Harg($R_3$)—OH;

As a preferred solution of the invention, when a Y fragment is coupled,
1) the Y fragment is coupled directly at once, and the Fmoc-protected amino acid or fragment is Fmoc-Gly-Asp(OtBu)-OH; or
2) the Y fragment is coupled successively at twice, and the Fmoc-protected amino acid or fragment is Fmoc-Asp(OtBu)-OH for the first time and Fmoc-Gly-OH for the second time.

When other fragments except X and Y are coupled in the invention, protected amino acids are respectively Fmoc-Trp ($R_1$)—OH with $R_1$ being Boc or H, Fmoc-Pro-OH, and Fmoc-Cys($R_2$)—OH with $R_2$ being Trt or Acm.

As a preferred solution of the invention, when each amino acid or fragment is coupled, the dosage of the protected amino acid is 1.2-6 times of the total mole number the carrier resin, preferably 3 times.

The amino resin of the invention has an amino substitution value of 0.3-1.5 mmol/g, preferably 0.5-1.0 mmol/g.

Further, the amino resin is selected from one of Rink Amide resin, Rink Amide AM resin, Rink MBHA resin and Sieber resin, preferably Rink Amide MBHA resin.

Rink Amide AM resin

-continued

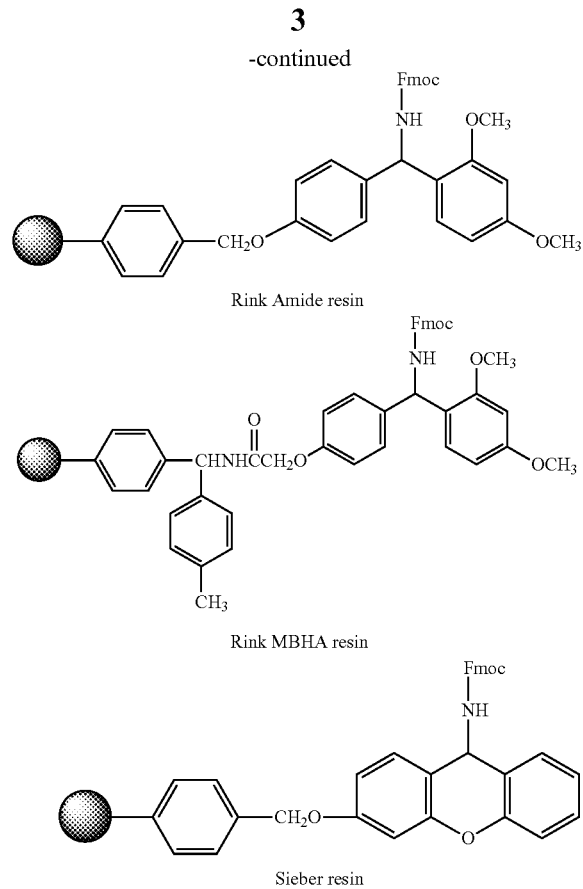

Rink Amide resin

Rink MBHA resin

Sieber resin

As a preferred solution of the invention, the solid phase coupling synthesis is as follows: the protected amino acid-resin obtained by the previous reaction is subject to Fmoc deprotection and participates in the coupling reaction with the next protected amino acid, with coupling reaction time of 60-300 min, preferably 100-140 min.

As a preferred solution of the invention, the crude linear peptide eptifibatide is obtained by acidolysis of the eptifibatide resin and removal of the resin and side chain protecting group:

Mpr-Harg-Gly-Asp-Trp-Pro-Cys-NH$_2$ (SEQ ID NO:1)

Further, the acidolysis agent for acidolysis of the eptifibatide resin is mixed solvent of trifluoroacetic acid (TFA), 1,2-dithioglycol (EDT) and water, and the ratio of the mixed solvent is as follows: the ratio of TFA is 80-95% (V/V), the ratio of EDT is 1-10% (V/V) and the remainder is water.

More preferably, the ratio is 89-91% for TFA, 4-6% for EDT and the remainder for water. Most preferably, the ratio is 90% for TFA, 5% for EDT and the remainder for water.

In 1 g eptifibatide, the dosage of the acidolysis agent is required to be 4-15 ml, and preferably, 1 g eptifibatide resin requires 9-11 ml acidolysis agent.

The cracking time of the acidolysis agent is 1-5 h at room temperature, preferably 2 h.

Further, the crude linear peptide eptifibatide is dissolved with acetic acid, then the dissolved crude linear peptide eptifibatide is filtered, oxidized and cyclized with an oxidant to obtain crude eptifibatide.

Sulfhydryl SH in Mpr of the linear peptide eptifibatide structure and SH in Cys are oxidized to form disulfide bond S—S to obtain Mpr-Harg-Gly-Asp-Trp-Pro-Cys-NH$_2$ (SEQ ID NO:1).

The volume percent concentration of acetic acid is 20-40%, preferably 30%.

The oxidant is iodine, H$_2$O$_2$ or DMSO, preferably iodine. The oxidant is added in a titration manner up to reaction end point.

Further, pure eptifibatide is obtained by purification of crude eptifibatide by high performance liquid chromatography, salt exchange and lyophilization.

In the method of the invention, fragments containing protected amino acids are directly used to prepare eptifibatide, thus directly avoiding the generation of impurities such as [+1Gly]-eptifibatide, [−1Gly]-eptifibatide and [−1Harg]-eptifibatide, significantly reducing difficulty in purification, and ensuring product purity. The resulting product has a purity more than 99.5% and a single impurity of less than 0.2%. Compared with the prior art, the invention is characterized by simple reaction operation and mild reaction conditions, thus having extensive practical value and application prospect.

DESCRIPTION OF THE PREFERRED EMBODIMENTS

The preparation method of eptifibatide of the invention comprises preparation of eptifibatide resin by a solid phase polypeptide synthesis method, acidolysis and oxidation of the eptifibatide resin to obtain crude linear peptide eptifibatide, oxidation of the crude linear peptide eptifibatide to obtain crude eptifibatide, and purification of the crude eptifibatide to obtain pure eptifibatide, wherein the method for preparing the eptifibatide resin by the solid phase polypeptide synthesis method comprises successively coupling Fmoc-protected amino acids corresponding to the following sequence on amino resin through a solid phase coupling synthesis method to obtain the eptifibatide resin:

X—Y-Trp(R$_1$)-Pro-Cys(R$_2$)-amino resin where,
R$_1$ is Boc or H;
R$_2$ is Trt or Acm;
X is Mpr(R$_2$)-Harg(R$_3$), R$_3$ is Pbf or H; and
Y is Gly-Asp(OtBu).

As a preferred solution of the invention, the solid phase coupling synthetic reaction is carried out once only to couple an X fragment, and the Fmoc-protected amino acid or fragment for coupling is Mpr(Trt)-Harg(R$_3$)—OH;

As a preferred solution of the invention, when a Y fragment is coupled,
1) the Y fragment is coupled directly at once, and the Fmoc-protected amino acid or fragment is Fmoc-Gly-Asp(OtBu)-OH; or
2) the Y fragment is coupled successively at twice, and the Fmoc-protected amino acid or fragment is Fmoc-Asp(OtBu)-OH for the first time and Fmoc-Gly-OH for the second time.

When other fragments except X and Y are coupled in the invention, protected amino acids are:
Fmoc-Trp(R$_1$)—OH with R$_1$ being Boc or H, Fmoc-Pro-OH, and Fmoc-Cys(R$_2$)—OH with R$_2$ being Trt or Acm.

Where, the Fmoc is 9-fluorenylmethoxycarbonyl, tBu is tertiary butyl, Acm is acetamidomethy, OtBu is tert-butoxy, and Boc is tert-butoxycarbonyl group.

In the invention, the dosage of the protected amino acid is 1.2-6 times of the total mole number of the fed resin, preferably 3 times.

In the invention, the solid phase coupling synthesis is as follows: the protected amino acid-resin obtained by the previous reaction is subject to Fmoc deprotection and participates in the coupling reaction with the next protected amino acid. The Fmoc deprotection reagent is 10-30%(V/V) piperidine (PIP)/N,N-dimethylformamide (DMF) solution, preferably 20%(V/V). In 1 g fed resin, the dosage of the deprotection reagent is 5-15 ml, preferably 10 ml. The deprotection reaction time is 10-60 min, preferably 15-25 min.

A condensing reagent and activating reagent are added during the coupling. The condensing reagent is selected from N,N-diisopropylcarbodiimide (DIC), N,N-dicyclohexylcarbodiimide (DCC), benzotriazole-1-yl-oxy-tris-pyrrolidino-phosphonium hexafluorophosphate (PyBOP), 2-(7-aza-1H-benzotriazole-1-yl)-1,1,3,3-tetramethyluronium hexafluorophosphate (HATU), benzotriazole-N,N,N',N'-tetramethyluroniumhexafluophosphate (HBTU) or O-benzotriazole-N,N,N',N'-tetramethyluronium tetrafluobate (TBTU), preferably N,N-diisopropylcarbodiimide (DIC). The molar dosage of the condensing reagent is 1.2-6 times of total mole number of amino groups in amino resin, preferably 2.5-3.5 times.

The activating reagent is selected from 1-hydroxybenzotriazole (HOBt) and N-hydroxy-7-aza-benzotriazole (HOAt), preferably 1-hydroxybenzotriazole (HOBt).

The dosage of the activating reagent is 1.2-6 times of total mole number of amino groups in the amino resin, preferably 2.5-3.5 times.

The coupling reaction time is 60-300 min, preferably 100-140 min.

As a preferred solution of the invention, the amino resin has an amino substitution value of 0.3-1.5 mmol/g, preferably 0.5-1.0 mmol/g.

Further, the amino resin is selected from one of Rink Amide resin, Rink Amide AM resin, Rink MBHA resin and Sieber resin, preferably Rink Amide MBHA resin.

Further, the crude linear peptide eptifibatide is obtained by acidolysis of the eptifibatide resin and removal of the resin and side chain protecting group:

Mpr-Harg-Gly-Asp-Trp-Pro-Cys-NH$_2$ (SEQ ID NO:1)

The acidolysis agent for acidolysis of the eptifibatide resin is mixed solvent of trifluoroacetic acid (TFA), 1,2-dithioglycol (EDT) and water, and the ratio of the mixed solvent is as follows: the ratio of TFA is 80-95% (V/V), the ratio of EDT is 1-10% (V/V) and the remainder is water. More preferably, the ratio is 89-91% for TFA, 4-6% for EDT and the remainder for water. Most preferably, the ratio is 90% for TFA, 5% for EDT and the remainder for water.

In 1 g eptifibatide, the dosage of the acidolysis agent is required to be 4-15 ml, and preferably, 1 g eptifibatide resin requires 9-11 ml acidolysis agent.

The cracking time of the acidolysis agent is 1-5 h at room temperature, preferably 2 h.

Further, the crude linear peptide eptifibatide is dissolved with acetic acid, then the dissolved crude linear peptide eptifibatide is filtered, oxidized and cyclized with an oxidant to obtain crude eptifibatide.

The volume percent concentration of acetic acid is 20-40%, preferably 30%.

The oxidant is iodine, $H_2O_2$ or DMSO, preferably iodine. The oxidant is added in a titration manner up to reaction end point.

Further, pure eptifibatide is obtained by purification of crude eptifibatide by high performance liquid chromatography, salt exchange and lyophilization, the purification method comprises the following steps:

Crude eptifibatide powder is weighed, added to a proper amount of 30% acetic acid aqueous solution, and stirred to dissolve, and the resulting solution is filtered by 0.45 μm hybrid microporous filter membrane for subsequent use.

Chromatographic packing for purification by high performance liquid chromatography is 10 μm reversed phase C18, mobile phase for purification is 0.1% TFA/aqueous solution-0.1% TFA/acetonitrile solution, flow rate of a 77 mm*250 mm chromatographic column is 90 ml/min, and a gradient system is used for elution and purification by cycle sample injection. Supernatant of the crude eptifibatide solution is added to the chromatographic column, the mobile phase is started for elution and vacuum concentration in water bath below 40° C., and most of the acetonitrile is evaporated by a rotary evaporator to obtain purified eptifibatide concentrate, and the resulting purified eptifibatide concentrate is filtered by 0.45 μm filter membrane for subsequent use.

Chromatographic packing for salt exchange by high performance liquid chromatography is 10 μm reversed phase C18, mobile phase system for salt exchange is 1% acetic acid/aqueous solution-1% acetic acid/acetonitrile solution system, flow rate of a 77 mm*250 mm chromatographic column is 90 ml/min, and a gradient system is used for elution and salt exchange by cycle sample injection. Supernatant of the purified concentrate is added to the chromatographic column, the mobile phase is started for elution, then desalination main peak solution is collected and combined for vacuum concentration in water bath below 40° C., and most of the acetonitrile is evaporated by a rotary evaporator to obtain eptifibatide acetate aqueous solution which is lyophilized to obtain the product.

According to the invention, a fragment of the protected amino acids is directly used to prepare eptifibatide, with the purity more than 99.5% and the single impurity less than 0.2%. Compared with the prior art, the invention is characterized by simple reaction operation and mild reaction conditions, thus having extensive practical value and application prospect.

The following examples will be helpful for understanding the invention, but should not be construed as limit thereto.

Example 1

Synthesis of Fmoc-Gly-Asp(OtBu)-OH

First, 3.0 mol Fmoc-Gly-OH and 3.0 mol HOBt were dissolved with proper amount of DMF; then another 3.0 mol DIC was slowly added to protected amino acid DMF solution while stirring, and stirred at the room temperature for reaction for 30 min to obtain activated protected amino acid solution.

First, Fmoc-Asp(OtBu)-2-Cl-Trt-resin with total mole number of 1.0 mmol/g was subject to Fmoc deprotection using 5 L 20% PIP/DMF solution for 25 min, then the resin was washed respectively with MDF and DCM for three times after filtration, the protected amino acid solution was added and stirred at the room temperature for reaction for 3 h, then the resin was washed respectively with MDF and DCM for three times after filtration upon completion of the reaction, and dried to prepare Fmoc-Gly-Asp(OtBu)-2-Cl-Trt-resin.

The Fmoc-Gly-Asp(OtBu)-2-Cl-Trt-resin was added to 20 L 30% hexafluoroisopropanol/DCM solution and stirred for reaction for 2 h, then the filtrate was collected after filtration, and the solvent was dried by distillation under vacuum to obtain 446 g Fmoc-Gly-Asp(OtBu)-OH, with the yield of 95.2%, the purity of 98.3%, and MS m/z of 469 (M+1).

Example 2

Synthesis of Mpr(Trt)-Harg-OH

First, 3.0 mol Mpr(Trt)-OH and 3.0 mol HOBt were dissolved with proper amount of DMF; then another 3.0 mol DIC was slowly added to protected amino acid DMF solution while stirring, and stirred at the room temperature for reaction for 30 min to obtain activated protected amino acid solution.

First, Fmoc-Harg-2-Cl-Trt-resin with total mole number of 1.0 mmol/g was subject to Fmoc deprotection using 5 L 20% PIP/DMF solution for 25 min, then the resin was washed respectively with MDF and DCM for three times after filtration, the protected amino acid solution was added and stirred at the room temperature for reaction for 3 h, then the resin was washed respectively with MDF and DCM for three times after filtration upon completion of the reaction, and dried to prepare Mpr(Trt)-Harg-2-Cl-Trt-resin.

The Mpr(Trt)-Harg-2-Cl-Trt-resin was added to 20 L 30% hexafluoroisopropanol/DCM solution and stirred for reaction for 2 h, then the filtrate was collected after filtration, and the solvent was dried by distillation under vacuum to obtain 483 g Mpr(Trt)-Harg-OH, with the yield of 93.1%, the purity of 98.9%, and MS m/z of 520 (M+1).

Example 3

Synthesis of Eptifibatide Resin

The eptifibatide resin was:

X—Y-Trp($R_1$)-Pro-Cys($R_2$)-amino resin where, $R_1$ is Boc, $R_2$ is Trt, X is Mpr($R_2$)-Harg($R_3$), $R_3$ is H, and Y is Gly-Asp(OtBu).

Rink MBHA resin was successively coupled with the protected amino acids shown in Table 1 to obtain eptifibatide resin. The protected amino acids corresponding to the $1^{st}$ to $5^{th}$ amino acids from the resin of the protected amino acids used in the example are as follows:

TABLE 1

| Peptide coupling sequence n = | Protected amino acids | Molecular weight |
| --- | --- | --- |
| 1 | Fmoc-Cys(Trt)-OH | 586 |
| 2 | Fmoc-Pro-OH | 337 |
| 3 | Fmoc-Trp(Boc) | 526 |
| 4 | Fmoc-Gly-Asp(OtBu)-OH | 468 |
| 5 | Mpr(Trt)-Harg-OH | 519 |

Wherein, the $4^{th}$ protected amino acid is Fmoc-Gly-Asp(OtBu)-OH prepared in example 1, and the $5^{th}$ protected amino acid is Mpr(Trt)-Harg-OH prepared in example 2.

The activation method of the protected amino acid comprises the following steps:

First, 1.5 mol protected amino acid and 1.5 mol HOBt were dissolved with proper amount of DMF; another 1.5 mol DIC was slowly added to protected amino acid DMF solution while stirring, and stirred at the room temperature for reaction for 30 min to obtain activated protected amino acid solution.

The Rink MBHA resin with total mole number of 0.5 mmol was swelled with 5 L 20% piperidine (PIP)/NN-dimethylformamide (DMF) solution for 10 min, then 5 L 20% PIP/DMF solution was added after filtration and stirred at the room temperature for reaction for 25 min, then the resin was washed respectively with DMF and DCM for three times after filtration, added to the first activated protected amino acid solution for coupling reaction for 60-300 min, after the first amino acid was coupled, the resin was subject to Fmoc deprotection using 5 L 20% PIP/DMF solution for 25 min, filtered and washed for coupling reaction with the second activated protected amino acid solution for 60-300 min, and then filtered and washed to obtain 2-peptide resin.

The Fmoc-protected amino acids corresponding to the $3^{rd}$ to $5^{th}$ amino acids were successively coupled by the same method, then filtered and washed to obtain the eptifibatide resin.

Example 4

Acidolysis of Eptifibatide Resin

The eptifibatide resin prepared in example 7 was mixed with a cracking reagent [TFA/water/EDT=95:5:5 (V/V) (approximately 10 ml/g resin), and evenly stirred at the room temperature for reaction for 3 h, then a sand core funnel was used for filtering the reaction mixture, and the filtrate was collected, then the resin was washed with small amount of TFA for three times, the filtrates were combined and concentrated under vacuum, anhydrous ether was added for precipitation, and the precipitate was washed with anhydrous ether three times, and dried to obtain white powder that is crude linear peptide eptifibatide.

Example 5

Preparation of Crude Eptifibatide

The crude linear peptide eptifibatide prepared in example 3 was dissolved with 30% acetic acid solution and prepared into 0.5-5 mg/ml solution, then iodine/ethanol saturated solution was added dropwise while stirring until the solution was brownish red, stirred for reaction for 30 min, and Vc solution was added dropwise until the brownish red disappeared for vacuum concentration at 40° C. to obtain a crude eptifibatide concentrate.

Example 6

Preparation of Eptifibatide

1) Purification by High Performance Liquid Chromatography

The crude eptifibatide concentrate was filtered by 0.45 m hybrid microporous filter membrane for subsequent use. The mobile phase A was 0.1% TFA/aqueous solution, the mobile phase B was 0.1% TFA/acetonitrile solution, flow rate of a 77 mm*250 mm C18 chromatographic column was 90 ml/min, and gradient elution conditions as shown in Table 2 were used for purification by cycle sample injection. Supernatant of the crude bivalirudin solution was added to the chromatographic column, the mobile phase was started for elution, then the main peak was collected and acetonitrile was removed to obtain a purified eptifibatide concentrate.

TABLE 2

| Time | Mobile phase B |
| --- | --- |
| 00→05.0 min: | 5% |
| 00→5.0 min: | 0%→18% |
| 05→45.0 min: | 18%→25% |
| 45→55.0 min: | 25%→90% |
| 55→60.0 min: | 90% |
| 60→70.0 min: | 90%→18% |
| 70→80.0 min: | 5% |

2) Salt Exchange by High Performance Liquid Chromatography

The purified eptifibatide concentrate was filtered by 0.45 m filter membrane for subsequent use. High performance liquid chromatography was used for salt exchange, the mobile phase A was 1% acetic acid/aqueous solution, the mobile phase B was 1% acetic acid/acetonitrile solution, flow rate of a 77 mm*250 mm C18 chromatographic column was 90 ml/min, and gradient elution conditions as shown in Table 3 were used for salt exchange by cycle sample injection. Supernatant of the concentrate to be subject to salt exchange was added to the chromatographic column, the mobile phase was started for elution, the salt exchange main peak was collected and the purity was determined by analytical liquid chromatography, the salt exchange main peak solution was combined for vacuum concentration in water bath below 40° C., and most of the acetonitrile was evaporated by a rotary evaporator to obtain eptifibatide acetate aqueous solution.

TABLE 3

| Time | Mobile phase B |
|---|---|
| 00→05.0 min: | 5% |
| 05→25.0 min: | 5%→10% |
| 25→30.0 min: | 10% |
| 30→40.0 min: | 10%→25% |
| 40→55.0 min: | 25% |
| 55→60.0 min: | 25%→5% |
| 60→70.0 min: | 5% |

The eptifibatide acetate aqueous solution was lyophilized to obtain 255 g product, with the total yield of 61.3%.

Molecular weight: 833 (100% M+H), specific rotation: −85.1°, moisture: 1.8%, acetic acid: 5.6%, purity: 99.8%, and maximum single impurity: 0.11%.

resin through a solid phase coupling synthesis method to obtain the eptifibatide resin:

X-Y-Trp($R_1$)-Pro-Cys($R_2$)-amino resin where,
$R_1$ is Boc or H;
$R_2$ is Trt or Acm;
X is Mpr($R_2$)-Harg($R_3$),
$R_3$ is Pbf or H; and
Y is Gly-Asp(OtBu).

2. The method according to claim 1, characterized in that the solid phase coupling synthetic reaction is carried out once only to couple an X fragment, the amino acid or fragment for coupling is Mpr(Trt)-Harg($R_3$)—OH, and $R_3$ is Pbf or H.

3. The method according to claim 1, wherein when a Y fragment is coupled,
 1) the Y fragment is coupled directly once, and the amino acid or fragment is Fmoc-Gly-Asp(OtBu)-OH; or
 2) the Y fragment is coupled successively a first time and a second time, and the amino acid or fragment is Fmoc-Asp(OtBu)-OH for the first time and Fmoc-Gly-OH for the second time.

4. The method according to claim 1, wherein when other fragments except X and Y are coupled, protected amino acids are Fmoc-Trp($R_1$)—OH with $R_1$ being Boc or H, Fmoc-Pro-OH, and Fmoc-Cys($R_2$)—OH with $R_2$ being Trt or Acm.

The invention claimed is:

1. A method of preparing eptifibatide, comprising the steps of:
 preparation of eptifibatide resin by a solid phase polypeptide synthesis reaction,
 acidolysis of the eptifibatide resin to obtain crude linear peptide eptifibatide,
 oxidation of the crude linear peptide eptifibatide to obtain crude eptifibatide, and
 purification and salt exchange of the crude eptifibatide to obtain finished eptifibatide,
 wherein the step for preparing the eptifibatide resin by the solid phase polypeptide synthesis reaction comprises successively coupling a protected amino acid or fragment corresponding to the following sequence on amino 5. The method according to claim 1, wherein when each fragment of amino acids is coupled, dosage of the protected amino acids is 1.2-6 times of a total mole number of carrier resin.

6. The method according to claim 5, wherein the dosage of the protected amino acids is 3 times the total mole number of the carrier resin.

7. The method according to claim 1, wherein the amino resin has a substitution value of 0.3-1.5 mmol/g.

8. The method according to claim 7, wherein the amino resin has a substitution value of 0.5-1.0 mmol/g.

9. The method according to claim 7, wherein the amino resin is a member selected from the group consisting of Rink Amide resin, Rink Amide AM resin, Rink MBHA resin and Sieber resin.

10. The method according to claim 9, wherein the amino resin is Rink Amide MBHA resin.

11. The method according to claim 1, wherein the solid phase coupling synthesis reaction comprises subjecting the protected amino acid or fragment to Fmoc deprotection to provide a deprotected amino acid or fragment which participates in the coupling reaction with the next protected amino acid, with coupling reaction time being 60-300 min.

12. The method according to claim 11, wherein the coupling reaction time is 100-140 min.

13. The method according to claim 1, wherein the crude linear peptide eptifibatide is obtained by acidolysis of the eptifibatide resin and removal of the following resin and side chain protecting group:

Mpr-Harg-Gly-Asp-Trp-Pro-Cys-$NH_2$    (SEQ ID NO:1).

14. The method according to claim 13, wherein an acidolysis agent for acidolysis of the eptifibatide resin is a mixed solvent of 80-95% (V/V) trifluoroacetic acid (TFA), 1-10% (V/V) 1,2-dithioglycol (EDT) and water.

15. The method of according to claim 1, wherein when the crude eptifibatide is obtained by oxidation of the crude linear peptide eptifibatide, the crude linear peptide eptifibatide is dissolved with acetic acid, then the dissolved crude linear peptide eptifibatide is filtered, oxidized and cyclized with an oxidant, and sulfhydryl SH in Mpr of the linear peptide eptifibatide structure and SH in Cys are oxidized to form disulfide bond S—S to obtain Mpr-Harg-Gly-Asp-Trp-Pro-Cys-$NH_2$ (SEQ ID NO:1), and the oxidant is at least one of iodine, $H_2O_2$ or DMSO.

* * * * *